(12) United States Patent
Lu et al.

(10) Patent No.: US 8,523,756 B2
(45) Date of Patent: Sep. 3, 2013

(54) CARDIAC COMPRESSION SYSTEM

(75) Inventors: Pong-Jeu Lu, Tainan (TW); Pao-Yen Lin, Tainan (TW); Jiin-Huey Chern Lin, Winnetka, IL (US); Chien-Ping Ju, Kansas City, MO (US)

(73) Assignee: National Cheng Kung University, Tainan (TW)

( * ) Notice: Subject to any disclaimer, the term of this patent is extended or adjusted under 35 U.S.C. 154(b) by 454 days.

(21) Appl. No.: 12/818,645

(22) Filed: Jun. 18, 2010
(Under 37 CFR 1.47)

(65) Prior Publication Data
US 2010/0256441 A1    Oct. 7, 2010

(30) Foreign Application Priority Data

Dec. 31, 2008  (US) .................................... 08/88620

(51) Int. Cl.
*A61N 1/362*     (2006.01)
(52) U.S. Cl.
USPC .............................................. 600/16; 600/37
(58) Field of Classification Search
USPC ........................................... 600/16, 37
See application file for complete search history.

(56) References Cited

U.S. PATENT DOCUMENTS

| | | | |
|---|---|---|---|
| 4,573,997 A | 3/1986 | Wisman et al. | |
| 4,690,134 A * | 9/1987 | Snyders | 601/153 |
| 4,731,073 A | 3/1988 | Robinson | |
| 4,888,011 A | 12/1989 | Kung et al. | |
| 5,131,905 A | 7/1992 | Grooters | |
| 5,332,403 A | 7/1994 | Kolff | |
| 5,910,124 A | 6/1999 | Rubin | |
| 5,928,132 A | 7/1999 | Leschinsky | |
| 6,146,325 A | 11/2000 | Lewis et al. | |
| 6,432,039 B1 | 8/2002 | Wardle | |
| 6,540,666 B1 | 4/2003 | Chekanov | |
| 7,066,874 B2 | 6/2006 | Riebman et al. | |

(Continued)

FOREIGN PATENT DOCUMENTS

| | | |
|---|---|---|
| JP | 10-174713 A | 6/1998 |
| JP | 2002-532189 A | 10/2002 |

(Continued)

OTHER PUBLICATIONS

First Use of the TandemHeart Percutaneous Left Ventricular Assist Device article, 2 pages.

(Continued)

*Primary Examiner* — Christopher D Koharski
*Assistant Examiner* — Michael Carey
(74) *Attorney, Agent, or Firm* — Rosenberg, Klein & Lee

(57) ABSTRACT

The present direct cardiac compression (DCC) design, termed Cardiac Resynchronization Compression Sac System (CRCSS), combines the mechanical and electrical characteristics associated with DCC and cardiac resynchronization therapy (CRT), respectively. The CRCSS comprises a shell, at least one opening on the shell, at least one inflatable balloon, and a pumping system. The shell is custom manufactured to substantially conform to the contour of a portion of a heart, the contour being obtained by an imaging system. The opening on the shell is designed for passing pericardial fluid so as not to impede the myocardial contraction. The inflatable balloon attaches to at least one predetermined location of the inner surface of the shell. Furthermore, the shell naturally positions in the pericardium space without resorting to any artificial force to prevent it from dislodging from the heart. When the inflatable balloon inflates at least one ventricular free wall of the heart is compressed.

21 Claims, 6 Drawing Sheets

(56) References Cited

U.S. PATENT DOCUMENTS

| | | |
|---|---|---|
| 7,217,236 B2 | 5/2007 | Calderon et al. |
| 7,258,679 B2 | 8/2007 | Moore et al. |
| 7,269,460 B2 | 9/2007 | Chinchoy |
| 7,291,105 B2 * | 11/2007 | Lau et al. ............... 600/37 |
| 7,367,959 B2 | 5/2008 | Nardi |
| 2007/0005127 A1 | 1/2007 | Boekstegers et al. |
| 2007/0260108 A1 * | 11/2007 | Criscione ............... 600/16 |
| 2008/0300447 A1 | 12/2008 | Lu et al. |
| 2008/0306329 A1 | 12/2008 | Lu et al. |

FOREIGN PATENT DOCUMENTS

| | | |
|---|---|---|
| WO | 2004/112867 A1 | 12/2004 |
| WO | 2007089500 | 8/2007 |
| WO | 2008138956 | 11/2008 |
| WO | 2009088916 | 7/2009 |

OTHER PUBLICATIONS

Communication from European Patent Office dated Sep. 19, 2012.

* cited by examiner

CARDIAC COMPRESSION SYSTEM

CROSS REFERENCE TO RELATED APPLICATIONS

This application claims the benefit of PCT patent application serial no. PCT/US2008/088620, filed on Dec. 31, 2008, in the name of inventors Pong-Jeu Lu, Pao-Yen Lin, Jiin-Huey Chem Lin, and Chien-Ping Ju, which, in turn, claims the benefit of priority based on U.S. Provisional Patent Application Ser. No. 61/010,241, filed on Jan. 8, 2008, in the name of inventors Pong-Jeu Lu, Pao-Yen Lin, Jiin-Huey Chern Lin, and Chien-Ping Ju, the entire contents of PCT patent application and U.S. Provisional Patent Application are hereby incorporated by reference.

TECHNICAL FIELD

This present invention relates to a cardiac compression system, and more particularly, to a cardiac resynchronization compression sac system.

BACKGROUND

I. Direct Cardiac Compression

The concept of Direct Cardiac Compression (DCC) as a modality for circulation support comes from the emergent resuscitation of heart and lung. The most unique advantage of DCC, as compared to other existing Ventricular Assist Devices (VADs), lies in its non-blood contacting characteristic. By applying force directly to compress the decompressed heart, the extrinsic DCC devices help increase the ventricle contractile state and hereby improve the cardiac output. DCC can be fulfilled by, but not limited to, the following methods:

Skeletal Muscle Pump

This dynamic cardiomyoplasty method uses left latissimus dorsi muscle wrap to compress the decompensated heart. It takes time for muscle training and conversion, requiring patient condition be less emergent and have enough transition time for the muscle wrap to turn functional effective after surgery. Dynamic cardiomyoplasty met with difficulty in clinical trials and was terminated in the course of Phase III preparation due to insufficient patient recruitment. Major problems of muscle resistance to fatigue and the transformation of skeletal muscle into cardiac-like muscle were not satisfactorily resolved.

Mechanical Pumping Devices

This category comprises devices such as Anstadt Cup, CardioSupport System, Heart Booster, and HeartPatch, among others. Biocompatible material was used as the sac or cuff-like apparatus that deploys the externally applied compression forces. Fixation has been the major design concern of how the device is mounted onto the cardiac skin. Usually persistent suction power, glue adhesion or stay suture were used. Injurious complications include myocardial contusion, ischemia due to coronary artery compression, and frequent arrhythmias caused by asynchronous mechanical compression. To date, DCC devices can only be used in a short-term manner notwithstanding great effort has been tried to prolong the DCC usage period. HeartPatch DCC, however, uses separate, nonsurround patches placed on the ventricular free walls. The epicardial fusion adhesion was observed resulting from the tissue infusion of porous silicone material applied as the heart-contacting membrane. This fixation method avoids using persistent suction force and thus was intended for chronic use. All DCC devices showed effective enhancement in cardiac output. Nevertheless, the long-term efficacy has not been demonstrated and the complications that might arise due to improper fixation and epicardial actuation await further investigations.

Passive Mechanical Containment

This category of devices only provides restraining force to prevent further heart dilation. The avoidance of pathological enlargement of diseased heart was set as the design objective. Systolic enhancement has been critically limited by the small amount of elastic energy stored in the structural deformation of the sac in the diastolic phase. Acron Cardiac Support Device (CDS) is a representative apparatus. Acron CDS is an elastic textile net that wraps around both ventricles under the atrio-ventricular groove. It was found in chronic clinic trial that Acron net infused with the epicardium and thus caused myocardial fibrosis, leading to the impairment of cardiac contractility.

II. Cardiac Resynchronization Therapy

Cardiac resynchronization therapy (CRT) arises as a new and less traumatic treatment for congestive heart failure (CHF). About 30% CHF patients suffer dilated or ischemic cardiomyopathy, for which myocardial conduction delay manifests in the form of left bundle branch block and conduction heterogeneity have been the frequently observed symptoms. By way of electrical stimulation CRT can recoordinate contractile synchronization between left and right ventricles as well as among muscle segments within left ventricle (LV). Bi-ventricular and left ventricular pacing modes were found most effective in both acute studies and chronic CRT trials. Except for refractory advanced heart failure, conduction disordered patients who received CRT, in general, showed improvements in heart failure functional classification, quality of life and cardiac ejection fraction.

Acute hemodynamic improvements such as LV pressure gradient dp/dt increase, aortic pulse pressure elevation and averaged systolic pressure enhancement were observed upon acute ventricular pacing. A six-month chronic CRT trial tested on 25 patients indicates that left ventricle volume reduction occurred in a majority of patients with advanced heart failure. Similar large-scale random CRT test including 453 moderate-to-severe heart failure patients randomly divided into control and CRT groups also indicates benefits gained in hemodynamic performance and heart failure class function. Although studies in large patient cohorts with longer test periods are required to ascertain that CRT leads to cardiac reverse remodeling, the therapeutic outcome of reduced wall stress, myocardial oxygen consumption and mitral regurgitation already proved the general efficacy of CRT.

The pathologically enlarged cardiac chambers not only impair the myocardial contractility but also cause inhomogeneous inter- and intra-ventricular conduction delay, leading to inefficient use of muscle energy during cardiac contraction. Pacing with controlled atrioventricular conduction delay may reduce this asynchrony, literally at no expense of increased LV oxidative metabolism. Except for severely injured myocardium CRT can benefit some patients with elevated pulse pressure and intensity, manifested in terms of higher dp/dt in addition to gross symptom and ejection fraction improvements. The therapeutic rationale underlying this conduction recoordination is obvious. Myocardial contraction, which is the end point of electrical stimulation, could be resynchronized and hence functions in a more efficient manner to reduce the abnormal systolic workload and metabolic oxygen demand for the myocardium.

Electrophysiological alterations were frequently observed among advanced heart failure patients receiving chronic left ventricular assist device (LVAD) circulation support. It was reported that LVAD support resulted in immediate QRS interval decrease on the EKG waveform, indicating myocardial stress condition alteration. Moreover, QT interval, which reflects the repolarization of myocytes, shows an initial acute prolongation followed by a chronic shortening. Both QT prolongation and dispersion, and increased QRS duration are abnormal action potential characteristics associated with chronic heart failure. LVAD unloading, which immediately mitigates the pathological myocardial stretch due to excessive loading condition, may produce an acute inward current change across the ion channel, leading to the initial QT interval prolongation. Opposite myocardial repolarization behavior, however, appears in sustained cardiac unloading after weeks or months. It has been demonstrated in many LVAD unloaded patients that myocyte hypertrophy, ion homeostasis, cellular relaxation and adrenergic responsiveness were reversely remodeled. Although it is not clear whether those electrophysiological trend reversals were caused by shortened myocardium or by increased conduction velocity, mechanical unloading has consistently demonstrated its vital role in the reverse remodeling of LVAD-assisted failing hearts.

SUMMARY OF THE INVENTION

The design of the present "Cardiac Resynchronization Compression Sac System (CRCSS)" aims at avoiding the aforementioned drawbacks associated with those previously developed DCC devices. The present CRCSS is intended to provide therapeutic systolic assistance as well as diastolic containment in a long-term manner to support the advanced heart failure. Bridge-to-recovery is set as the design objective, which requires that the implanted device be chronically applied without complications and be conveniently removed at the end of support. Therefore, hard-fixation methods such as persistent vacuum suction, suture, and epicardial adhesion fixations were discarded because they do not serve the present design objective of long-term application and bridge-to-recovery. A new "soft-fixation" design concept is proposed instead, as stated in the following section.

The selection of the DCC enforcement location for the present CRCSS is motivated in part by the clinic results obtained in cardiac resynchronization therapy (CRT). For the present CRCSS device, ventricular free wall region is the place chosen for applying the epicadial compression forces. The applied compression force, hence, not only imparts mechanical energy into blood stream, but also works as a mechanical stimulus to resynchronize myocardial contraction and, hopefully, induce the electrophysiological reverse remodeling for the chronic diseased heart.

The present sac design is believed to play multiple roles in encouraging the diseased hearts to undergo reverse remodeling. Aside from passive mechanical containment achieved during diastolic period, the systolic support via epicardial compression may contribute to hemodynamic as well as electrophysiological trend reversals. The exertion of bi-ventricular compression at both right and left ventricular free walls would be of particular significance in the remedy of the conduction abnormalities, as implied in those electric CRT treatments. Mechanical and electrical behaviors of heart are mutually interactive. Except for refractory heart failure, by mechanically unloading a diseased heart, the action potential dysfunction associated with maladapted myocytes can be regressed toward a restored healthier state. Conversely, by a synchronous stimulation of myocardium, either inter-ventricularly or intra-ventricularly, the electric conduction renormalization can encourage a more homogeneous cardiac contraction, resulting in a higher mechanical contractile efficiency.

DCC enforcement, which comes by extraneously increasing the overall ventricular contraction force rather than by reducing the vascular afterload, equivalently, may create a milieu of myocardial unloading. In other words, despite the dissimilar forcing exertion, the reverse remodeling reflected in electrophysiological changes due to vascular afterload reduction observed in LVAD-supported group would also be expected to appear in patients with DCC assistance. Epicardial compression can effectively reduce or nullify the transmural tension over the epicardial area it contacts. Free wall DCC actuation can immediately relieve the myocardial stress condition around the most conduction-sensitive region, hence is hypothesized to be the best forcing scenario for DCC to stimulate therapeutic electrophysiologic renormalization which might lead to cellular reverse remodeling for the moderate diseased heart.

Pacing-type CRT may not rectify intra-ventricular conduction delay and dispersion for ventricles having infarcted myocardium with scarred tissue. Pacing-induced synchronous contraction, in principle, cannot be achieved when myocardial conduction network is damaged and the damaged part cannot be bypassed by extraneous route or by initiating another independent stimulation which ignores the zone of conduction block. Mechanical-type CRCSS, however, has no such restriction. As long as appropriate timing is scheduled for activating sac compression, the assisted myocardium will follow the EKG-referenced DCC forcing rhythm as a whole, no matter whether the conduction network is sound or not. Electrophysiological reverse remodeling, should it arise, is thereby taken as a value-added outcome rather than the causal factor of a resynchronized, stress relieved myocardial contraction when a heart is supported by the present CRCSS means.

The present CRCSS invention takes full advantage of these electromechanical interactions associated with the cardiac cellular behaviors. No matter viewed from mechanical or conduction perspective, ventricular free wall is the best candidate region for DCC application. In order to consistently hold CRCSS in position for precise bi-ventricular free wall compression, CRCSS requires a special forcing alignment and structural arrangement in which fixation design is essential. A soft-fitness strategy is considered herein, which is augmented by an EKG-referenced feedback control system. Special care was exercised in the CRCSS drive line and fluid supply control design, aiming at giving a synchronized, simultaneous right and left ventricular compression.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting, embodiments illustrated in the drawings, wherein like reference numbers (if they occur in more than one view) designate the same elements. The invention may be better understood by reference to one or more of these drawings in combination with the description presented herein.

DETAILED DESCRIPTION

CRCS Design Objectives and Embodiments

Figure 1A:
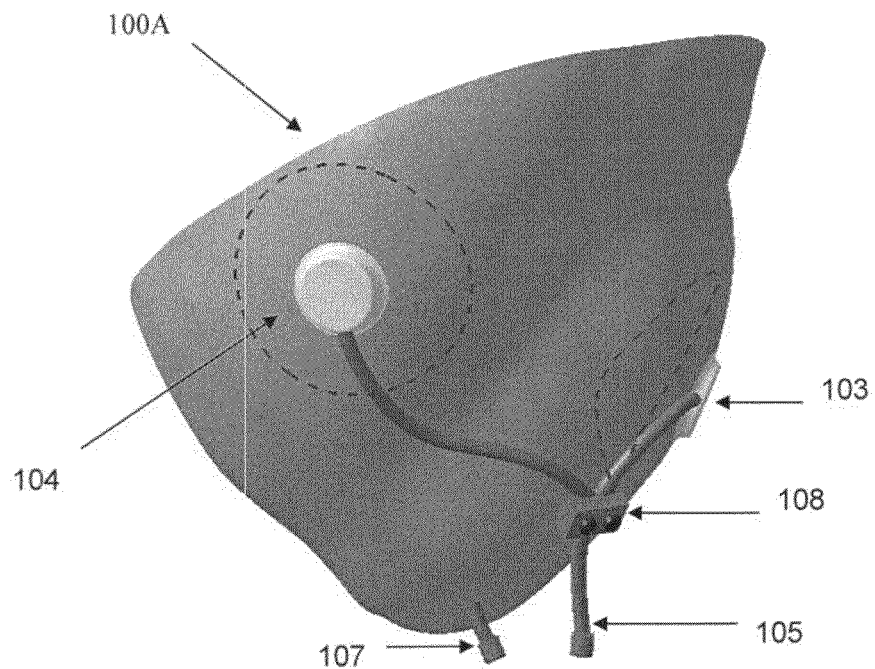
FIG. 1A shows the perspective view of one representative embodiment of the present invention (cardiac resynchronization compression sac, CRCS) and the constituent components.

Major issues associated with CRCS enforcement include fixation and synchronous sac actuation in response to heart contraction and relaxation. In order to stimulate electrophysiological reverse remodeling, pumping assist should be applied over the ventricular free wall region. The present CRCS design intends to deliver bi-ventricular epicardium compression in synchrony with the heart rhythm, for which atrioventricular conduction delay control and simultaneous right and left heart assistance are the design objectives to achieve. In the following, the fixation method and cardiac resynchronization pumping design are explained.

a. Soft-Fixation

Hard-fixation methods such as vacuum suction, glue adhesion and stay suture are excluded presently. Instead, a soft-fixation strategy which allows a non-interfering sac be snuggly placed around the heart is considered. Soft-fixation means a fixation that restricts or wraps the device around a target object with low contact pressure and minimal allowable clearance. By this definition, soft-fixation would not jeopardize the original functional objective when attaching a device onto its target object, nor will it induce undesirable side effects due to excessive tightness of contact created in installment. Wearing a pair of shoes is a good illustrative example. The shoes are intended to be put on the feet without interfering or hampering the function of walking. Appropriate space is kept between the shoe and the foot, which protects the foot from injurious contact and makes walking a pleasant experience. The clearance should not be too large so as to cause dislodging, nor too small so that it may invite compression or frictional contusion or ecchymoses. Configuration appropriateness and fitness, hence, stand out as the main subjects for pursuing a successful soft-fixation.

From cardiac anatomy it is observed that heart is surrounded by a fluid-filled porch, called pericardium. The natural space between the heart and the pericardium is the place where CRCS is intended to dwell. In the design of the present CRCS, a proper duplication of the heart morphology at the end of diastole holds the key in the pursuit of a successful soft-fixation. The shape and volume of CRCS should not impede the diastolic filling of both right and left ventricles. An a priori imaging of the heart anatomy before surgery using an imaging system [such as: X-ray, computed tomography (CT), magnetic resonance imaging (MRI) and ultrasound (preferred echocardiography)] could be helpful in mapping the diseased heart. The outer shell of CRCS is configured using a geometrically similar, but a bit larger, proportional form made from the imaged contour of the targeted heart. This extra space, in general 5 to 15 cc, created in between the native heart and the CRCS outer shell will be reserved for fitness adjustment, as explained later. The a priori conformal shape tailoring enables CRCS to be placed securely in the patient's chest cavity. Soft-fixation, therefore, can best be achieved when the dissected pericardium is sutured back, as close as possible in fitting with the cardiac anatomy, to embrace the CRCS implant. Sandwiching CRCS in between heart skin and pericardium makes pericardial space a natural cradle to house the implanted sac. Pericardial fluid will be generated in the process of healing and this interstitial fluid may work as a lubricant which protects the heart skin from injurious contact during sac actuation.

In constructing the CRCS outer shell, non-distensibility requirement guides the determination of the shell thickness. Usually a thickness of 0.2~1.5 mm is sufficient when, for instance, biocompatible polyurethane is considered as the sac material. This non-distensible, anatomically-fitted outer shell will help direct compression force inward toward the heart when external forcing is applied. Note that the constructed CRCS is deformable and shape conformal in general. During insertion, the sac would be stabilized in its most fitted orientation after a few pumping strokes. A suitable CRCS implant should not affect the diastolic filling which can be reflected from the venous return pressure. These automatic sac positioning and non-interfering support in relation to the heart function were observed in the animal experiments conducted in the inventors' laboratory. Optimal fitness can be fine tuned by adjusting the cushion fluid volume as guided by observing the peri-operational venous or atrial pressures pertaining to the left and right hearts.

Figure 1B:
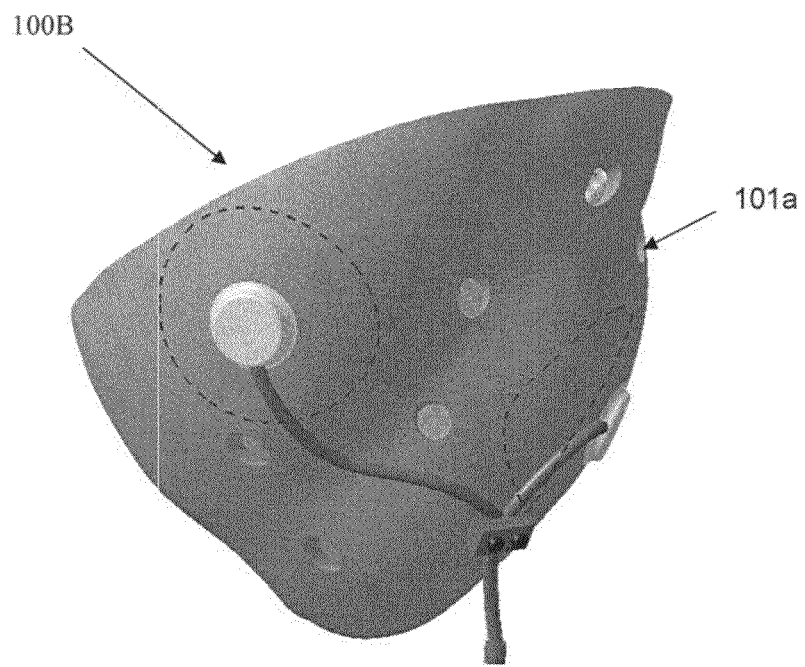
FIG. 1B shows the perspective view of another embodiment of the present invention (cardiac resynchronization compression sac, CRCS) and the constituent components.

FIGS. 1A and 1B show two possible embodiments of the present CRCS design 100A and 100B. The conical shape makes CRCS structurally reinforced around the apex. This hardened apex helps CRCS be easily inserted into the dissected pericardial space and is an ideal place for exiting the drive line 105. A Teflon cuff can be mounted around the connection site of the drive line to the sac. When closing the pericardium, this cuff can be sewn onto the pericardium, providing an additional guarantee to the soft-fixation.

Figure 3:
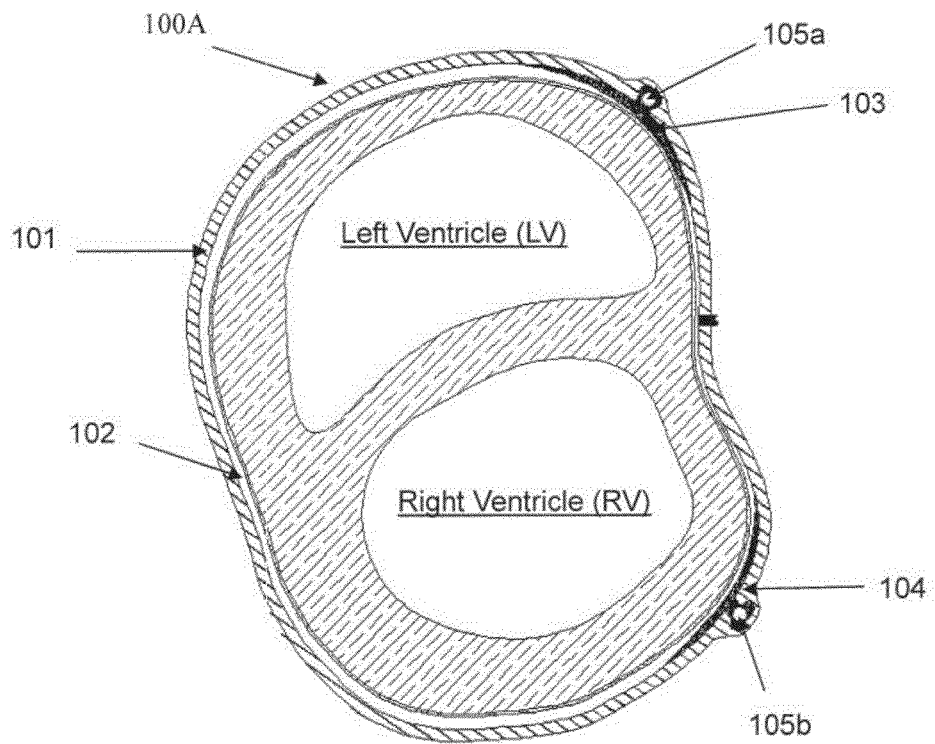
FIG. 3 shows the sectional view A-A of CRCS depicted in FIG. 1A at the end of diastole.
Figure 4:
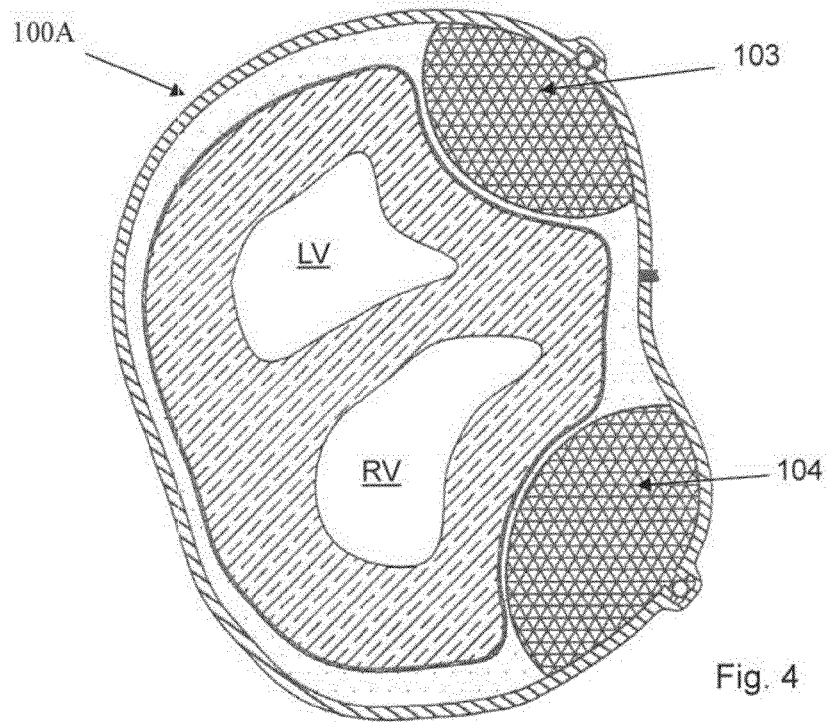
FIG. 4 shows the sectional view A-A of CRCS depicted in FIG. 1A during systole.
Figure 5:
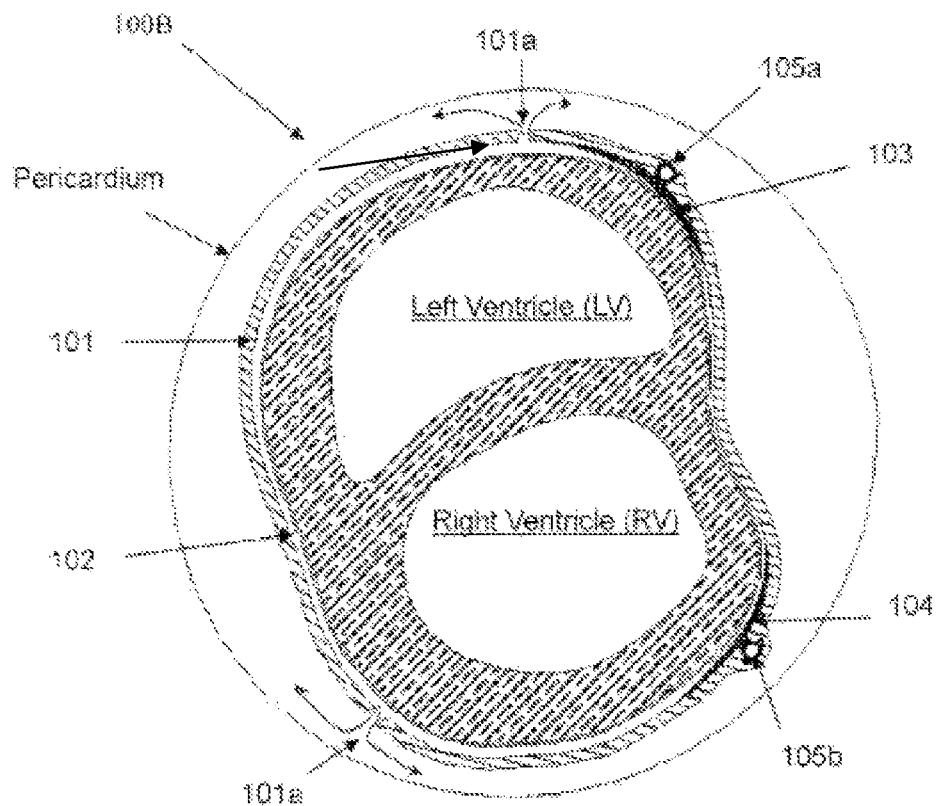
FIG. 5 shows the sectional view A-A of CRCS depicted in FIG. 1B at the end of diastole.
Figure 6:
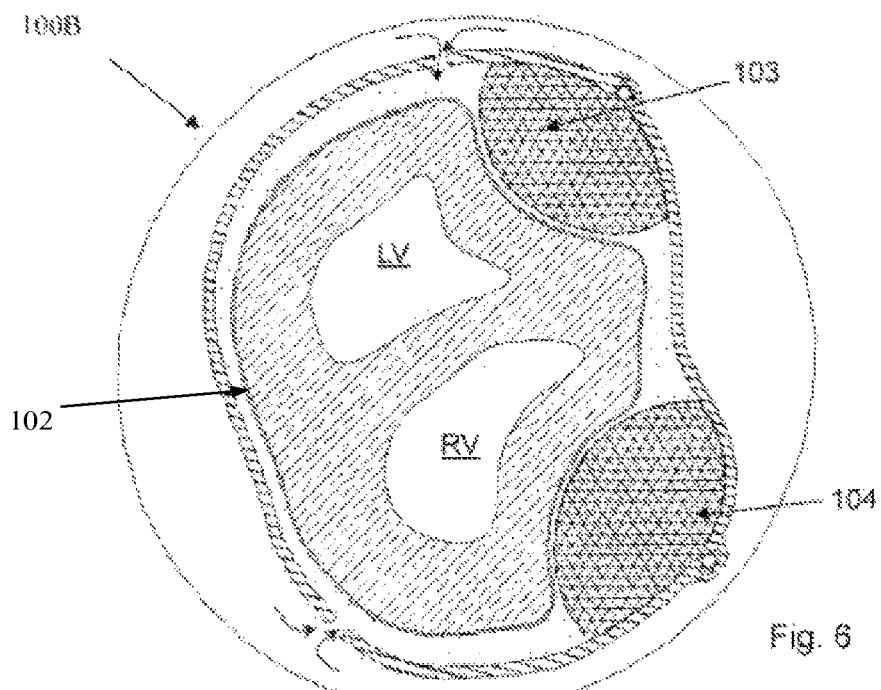
FIG. 6 shows the sectional view A-A of CRCS depicted in FIG. 1B during systole.

Similar image rendering and manufacturing process can be utilized to fabricate the inner diaphragm 102. The inner diaphragm 102 is thin in general, typically of a thickness about 10~100 micron. This shape-conformal, pliable diaphragm 102 may easily be attached onto the heart skin, in particular when inert polymeric material is used as the diaphragm material. Contrary to the previous DCC devices, the fluid (liquid or gas) contained in the space bounded by outer shell 101 and inner diaphragm 102 is not used as the direct force-transmitting medium. Rather, it serves as a buffer or a cushion which can be adjusted to achieve an optimal anatomic fitness either peri-operationally or post-operationally. A vent tube 107 and skin button assembly can be connected to the CRCS outer shell (see embodiment depicted in FIG. 1A), allowing extra-corporeal cushion fluid adjustment be performed whenever deemed necessary. FIGS. 3 and 4 further illustrate the relationship among pericardium, ventricles, CRCS diaphragm 102, balloons 103 and 104, and outer shell 101 in the systolic and diastolic phases, respectively. FIG. 1B depicts another embodiment which requires no cushion fluid adjustment. The openings 101a (such as perforations) punched through the outer shell make the pericardial fluid be freely communicated across the sac wall. This design permits an automatic cushion fluid adjustment be carried out on a beat-to-beat basis.

Ischemia complication has been reported for DCC application because epicardial compression may compress the coronary vascular bed during systolic assist. This complication can be mitigated by the present sac design. Except for the free wall region, the soft contact provided by non-pressurized diaphragm wrapping will leave most coronary arteries unaffected when compression force is applied.

b. Cardiac Resynchronization DCC Support

Figure 2:
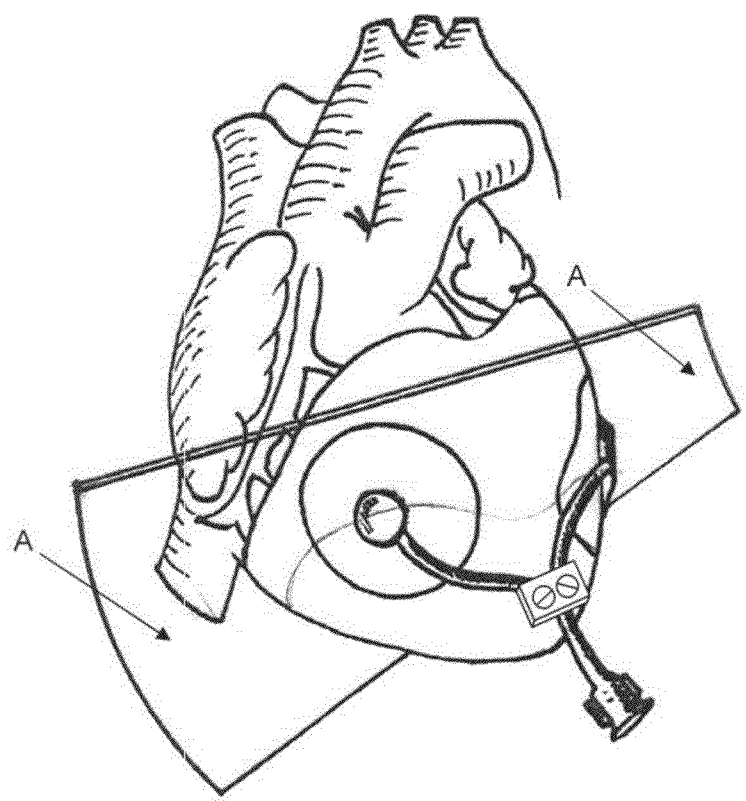
FIG. 2 shows the soft-fixation of CRCS as installed onto heart.

A pair of balloons 103 and 104 is used for DCC enforcement for the present CRCS design. FIG. 2 shows the positions of balloon placement in relation to the assisted heart morphology. These left and right balloons are hung on the inward side of the outer shell with their centroids aligned with the centers of the left and right ventricular free walls, respectively. The balloon stroke volume, 20~80 cc, can be selected depending on the cardiac condition specific to each patient at different implantation stages. A full capacity can be delivered in the initial assist phase to, for instance, increase the cardiac output required. However, as heart recovers with chamber volume and muscle mass decreased, the balloon stroke volume can be reduced accordingly, providing a progressive assist reduction for heart to wean off the sac support. The adjustment of the balloon stroke volume should particularly take into account the ventricular shrinkage effect. For instance, for the situation of a shrinking heart during recovery, a constant stroke volume pumping will gradually lose its DCC pumping effectiveness because the gap between the CRCS shell 101 and epicardium is enlarged. Whether or not the pumping stroke volume should be changed after CRCS implantation, in fact, depends on the patient's condition and the therapeutic plan designed by the physician.

The present balloon pumping is purposely designed to dispose the compression force over the most critical ventricular free wall area. Upon balloon actuation, the cushion fluid bounded between the outer shell 101 and the inner diaphragm 102 will redistribute to void the space displaced by balloon inflation. Since the stroke volume of heart is usually larger than that of the balloon, the further ventricular contraction beyond the CRCS stroke limit requires the influx of pericardial fluid to fill up the voided space although the inward movement of the outer shell 101 may account for some of the fluid volume adjustment. This collective cushion and pericardial fluid movement and shell deformation will make diaphragm an attached lining adjacent to the epicardium and hence avoid the otherwise undesired "diaphragm suction" phenomenon which may impede the myocardial shortening or ventricular chamber shrinkage during systolic ejection. The embodiment depicted in FIG. 1B is a preferred design which allows a quick epicardial fluid communication across the numerous CRCS shell openings 101a. Note that for FIG. 1A embodiment balloon moves against the sac diaphragm 102 rather than in direct contact with the heart skin, the relative movement resulting from DCC actuation and epicardial motion can thus be minimized. This unique feature can ameliorate frictional contusion and myocardial fibrosis due to long-term injurious contact of the moving sac relative to the epicardium.

It is worth noticing that the present CRCS intends to generate a kick-off type DCC support to assist the systolic contraction. Usually balloon stroke volume is set lesser than that of the ventricles, typically 20 to 50 percent of the natural stroke volume. Balloon actuation, as timed in conjunction with the QRS interval, will booster the contractile motion starting from the isovolumetric contraction to at most the peak ejection only. Epicardial compression assistance, hence, will diminish before maximum contraction is attained, leaving cardiac relaxation uninfluenced during heart diastole. Electrophysiologically, this may render repolarization of action potential be minimally interfered by the externally applied compression. Besides, kick-off type DCC support only unloads the heart at the initial myocardial shortening stage, and leaves heart contraction on its own beyond the kick-off boosting period. This partial support feature forms a natural rehabilitation mechanism that prevents heart from complete mechanical unloading which might be detrimental to the subsequent myocardial recovery and device weaning.

c. CRCS Pumping Control

External energy supply is required for pumping CRCS. Either extracorporeal or intracorporeal energy supply system can be considered. The differences lie in the working fluid and drive line 105 characteristics adopted. For the sake of convenience, extracorporeal pneumatic system with percutaneous drive line 105 will be used for illustrating the operational principles.

Consider an extracorporeal driving system equipped with a percutaneous drive line 105 is used to transport back and forth the pressurized fluid to and from the actuated balloons. Left and right balloons 103 and 104 may be actuated independently or collectively. For independent balloon driving (not shown in the figures), two percutaneous lines are required, each having its own pressure source and controller accompanied. Driving pressure level and synchronous pumping control can be facilitated individually in accordance with the left or right ventricle characteristics. For collective balloon driving, as shown in FIGS. 1A and 1B, however, only one set of drive line and controller system is equipped. The percutaneous drive line 105, after entering the chest cavity or pericardium, will bifurcate into left and right branches 105a and 105b, each shuttling the driving fluid respectively to the desired destination. Note that balloon pressurization depends on the inertia and resistance associated with the drive line 105 in addition to the reactant pressure exerted by the assisted ventricle wall. In order to achieve simultaneous bi-ventricular pumping, the lengths and lumen diameters of the right and left branches 105b and 105a ought to be properly tailored. This differential inertia/resistance design may allow a collective left and right heart assistance be executed in better synchrony with the heart contraction and relaxation.

The advantage associated with the single drive line 105 design is that it has only one percutaneous penetration and therefore minimizes the risk of post-operational infection complication. The disadvantage, however, lies in the control aspect because, for bi-ventricular assistance, optimal pumping level and peak pressure timing control for both left and right ventricles, in principle, cannot be achieved using only one pressure supply and timing control. The preferred CRCS embodiment adopts the single drive line 105 design as illustrated in FIGS. 1A and 1B. Sub-optimal control is set as the control objective to pursue. Pressure level and peak pressure timing will be determined primarily based on the left ventricle DCC requirements. Right heart control parameters, however, will be decided by tailoring the drive line 105 length and lumen diameter so as to attain the appropriate pumping pressure level and minimize the inconsistency between the systolic peak pressures associated respectively with the right and left heart support.

Figure 7:
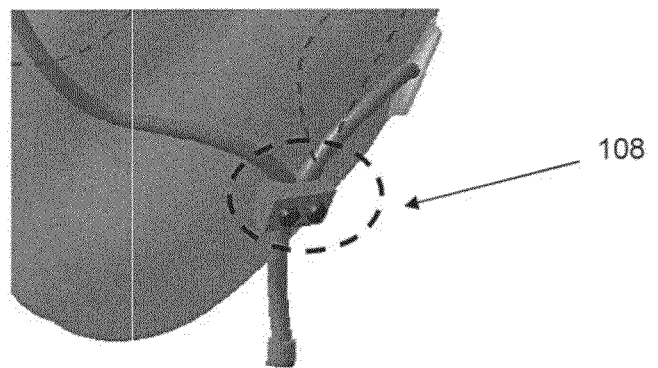
FIG. 7 shows the perspective, enlarged, and sectional perspective view B-B of drive line pressure regulator mounted on CRCS.
Figure 7:
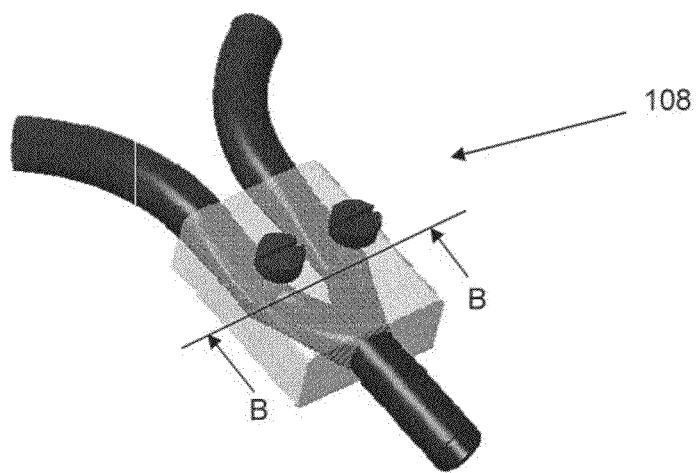
Figure 7:
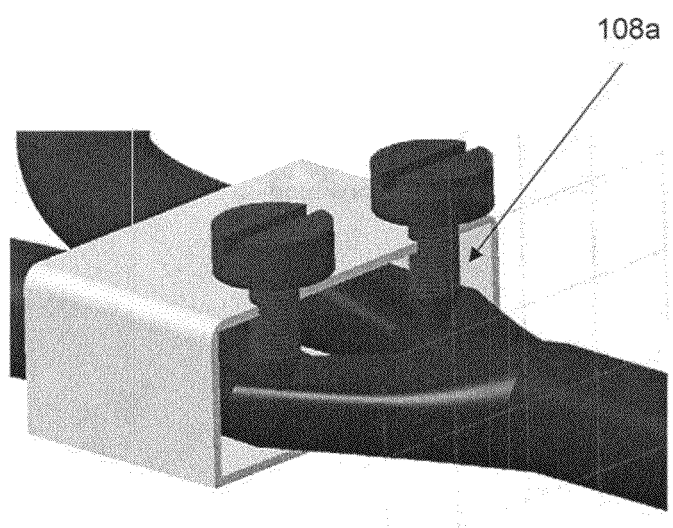

The fine tune of the pumping synchrony is accomplished using a pressure regulator 108 comprising a pair of pressure regulator screws 108a mounted on the bifurcation juncture of the drive line 105, as illustrated in FIG. 7. By squeezing or loosening the drive line lumen the delivered flow rate and pressure will change accordingly. In general, the left-and-right pumping synchrony is predetermined in an a priori analysis concerning the optimal assignment of differential right-left inertia/resistance parameters. Fine tune is carried out during sac implantation, which provides surgeon with a freedom in peri-operational adjustment to seek the optimal cardiac contractile synchrony.

Figure 8:
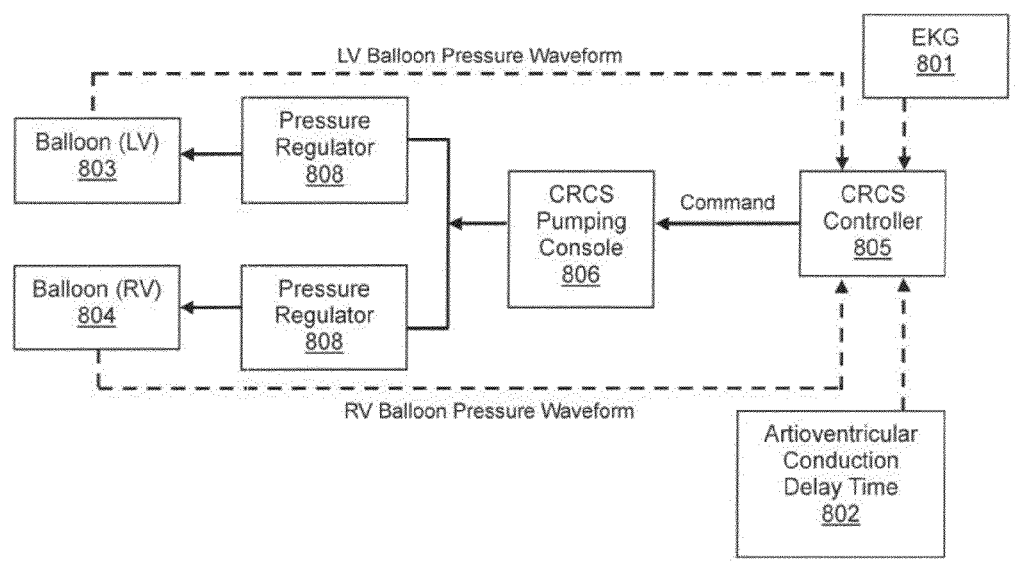
FIG. 8 shows the CRCS system control layout (the driver line, solid line; the control line, dashed line).

Synchronous pumping control design is shown in FIG. 8. Both left and right CRCS balloons 803 and 804 are equipped with pressure sensors. The pressure waveforms can be obtained and shown on the monitor during surgical operation. EKG signal 801 can also be obtained using, for instance, skin cathodes, and hence transmitted to the CRCS controller 805. Algorithm detecting R-wave and balloon pressure peaks will translate the right and left DCC assist into time delays relative to the R-wave. A scheduled atrioventricular conduction delay 802, electrically coupled with the CRCS controller 805, dictates the CRCS pumping console 806 in delivering the pressurized fluid to the actuation balloons. Right-and-left pumping synchrony will be manually controlled by adjusting the pressure regulator 108. The goal is to minimize the gap appearing on the systolic peaks pertaining to the right and left balloon pressure waveforms. For the present CRCS control design, unless specific concern arises, balloon stroke volume is predetermined and set fixed, typically selected in a range around 20~80 cc. The console driving pressure magnitude, hence, mainly controls the speed of balloon inflation. Hence, there will be no concern regarding the over-compression of the ventricles.

The joint enforcement of kick-off DCC and compliance to the heart rhythm helps realize the presently proposed soft-fixation concept. Kick-off support can minimize the fixation interference with the assisted heart and allow the cardiac muscle to contract, to a greater extent, according to its natural cardiac dynamics. This kick-off type DCC assist provided by the present CRCS design is believed to be a unique merit whose contribution is significant in promoting both mechanical and electrophysiological function recovery of a diseased heart.

What is claimed is:

1. A cardiac compression system comprising:
   a shell custom manufactured to substantially conform to the contour of a portion of a heart at the end of diastole, the contour of the heart being obtained by an imaging system;
   an elastic diaphragm coupled to an inner surface of the shell and defining a solid lining conforming to the heart;
   at least one opening on the shell for passing pericardial fluid; and
   at least one inflatable balloon attached to at least one predetermined location of the inner surface of the shell for selectively applying pressure to the heart at a specific ventricular location,
   wherein the shell is positionally retained in the pericardium space devoid of any fixed coupling to prevent it from dislodging from the heart, the at least one opening on the shell passing therethrough pericardial fluid disposed outside of the inflatable balloon, and the inflatable balloon inflates so as to compress at least one ventricular free wall of the heart at said specific ventricular location.

2. The cardiac compression system of claim 1, wherein the contour of the shell is substantially maintained.

3. The cardiac compression system of claim 1, wherein the shell has a conical shape for wrapping around the apex of the heart.

4. The cardiac compression system of claim 1, wherein the inflating volume of the at least one inflatable balloon is controllable.

5. The cardiac compression system of claim 1, wherein the inflation of the at least one inflatable balloon begins at a start of an isovolumetric contraction and ends before a peak ejection of the heart.

6. The cardiac compression system of claim 1, wherein the at least one inflatable balloon comprises a first and a second inflatable balloon for compressing a left and a right ventricular free wall, respectively.

7. The cardiac compression system of claim 6, wherein the inflating volume and timing of the first and second inflatable balloons are independently controllable.

8. The cardiac compression system of claim 6, wherein the inflating volume and timing of the first and second inflatable balloons are jointly controllable.

9. The cardiac compression system of claim 1, wherein the at least one inflatable balloon is inflated by a medium selected from a group consisting of a liquid and a gas.

10. The cardiac compression system of claim 1 wherein the elastic diaphragm has a contour similar to the shell, being attached to the rim of the inner surface of the shell and covering the inflatable balloon(s), wherein when the cardiac compression system is implanted, only the elastic diaphragm has substantial contact with the heart skin.

11. The cardiac compression system of claim 1, wherein the imaging system is selected from the group consisting of the following: X-ray, computed tomography (CT), magnetic resonance imaging (MRI) and ultrasound.

12. A cardiac compression system comprising:
    a shell custom manufactured to substantially conform to the contour of a portion of a heart at the end of diastole, the contour of the heart being obtained by an imaging system;
    at least one opening on the shell for passing pericardial fluid;
    at least one inflatable balloon attached to at least one predetermined location of the inner surface of the shell for selectively applying pressure to the heart at a specific ventricular location; and
    an elastic diaphragm defining a solid lining conforming to the heart and having a contour similar to the shell, the elastic diaphragm being attached to the rim of the inner surface of the shell and covering the at least one inflatable balloon,
    wherein the shell is positionally retained in the pericardium devoid of any fixed coupling to prevent it from dislodging from the heart, when the cardiac compression system is implanted, only the elastic diaphragm has substantial contact with the heart skin, the at least one opening on the shell passing therethrough pericardial fluid disposed outside of the inflatable balloon, and the at least one inflatable balloon inflates so as to compress at least one ventricular free wall of the heart at said specific ventricular location.

13. The cardiac compression system of claim 12, wherein the contour of the shell is substantially maintained.

14. The cardiac compression system of claim 12, wherein the shell has a conical shape for wrapping around the apex of the heart.

15. The cardiac compression system of claim 12, wherein the inflating volume of the at least one inflatable balloon is controllable.

16. The cardiac compression system of claim 12, wherein the inflation of the at least one inflatable balloon begins at a start of an isovolumetric contraction and ends before a peak ejection of the heart.

17. The cardiac compression system of claim 12, wherein the at least one inflatable balloon comprises a first and a second inflatable balloon for compressing a left and a right ventricular free wall, respectively.

18. The cardiac compression system of claim 17, wherein the inflating volume and timing of the first and second inflatable balloons are independently controllable.

19. The cardiac compression system of claim 17, wherein the inflating volume and timing of the first and second inflatable balloons are jointly controllable.

20. The cardiac compression system of claim 12, wherein the at least one inflatable balloon is inflated by a medium selected from a group consisting of a liquid and a gas.

21. The cardiac compression system of claim 12, wherein the imaging system is selected from the group consisting of the following: X-ray, computed tomography (CT), magnetic resonance imaging (MRI) and ultrasound.

* * * * *